(12) United States Patent
Purdy

(10) Patent No.: US 7,463,920 B2
(45) Date of Patent: Dec. 9, 2008

(54) RAPID MR VISUALIZATION OF INTERVENTIONAL DEVICES

(75) Inventor: David Embrey Purdy, Pearland, TX (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 257 days.

(21) Appl. No.: 11/089,804

(22) Filed: Mar. 25, 2005

(65) Prior Publication Data
US 2006/0241378 A1    Oct. 26, 2006

(51) Int. Cl.
*A61B 5/00* (2006.01)
*G01V 3/00* (2006.01)

(52) U.S. Cl. ........................ 600/424; 324/307

(58) Field of Classification Search ................. 600/410, 600/424; 324/307, 309, 313, 318, 320
See application file for complete search history.

(56) References Cited

U.S. PATENT DOCUMENTS

| | | | | |
|---|---|---|---|---|
| 5,708,359 A | * | 1/1998 | Gregory et al. | 324/309 |
| 6,400,157 B1 | * | 6/2002 | Bonanni et al. | 324/322 |
| 6,690,961 B1 | * | 2/2004 | Kaufman et al. | 600/410 |
| 7,071,690 B2 | * | 7/2006 | Butts et al. | 324/309 |
| 7,148,880 B2 | * | 12/2006 | Magara | 345/161 |

* cited by examiner

*Primary Examiner*—Eric F Winakur
*Assistant Examiner*—Michael T Rozanski
(74) *Attorney, Agent, or Firm*—Alexander J. Burke

(57) ABSTRACT

A method and apparatus for visualizing an interventional device in a body using a magnetic resonance (MR) imager. In operation an MR pulse sequence is applied to the body so as to develop MR signals, which are processed so as to acquire one or more images. An operator of the imager uses a hands-free device to control parameters of the applied pulse sequence so as to cause the images to show an intensity distortion artifact in the area of the interventional device that is increased as compared to intensity distortion artifact in conventional MR images; and, after an image distortion which is expected to be produced by the interventional device is seen, the operator changes the applied pulse sequence parameters, in a "hands-free" manner, so that said one or more acquired images show an intensity distortion artifact in the area of the interventional device that is reduced as compared to said increased intensity distortion.

16 Claims, 1 Drawing Sheet

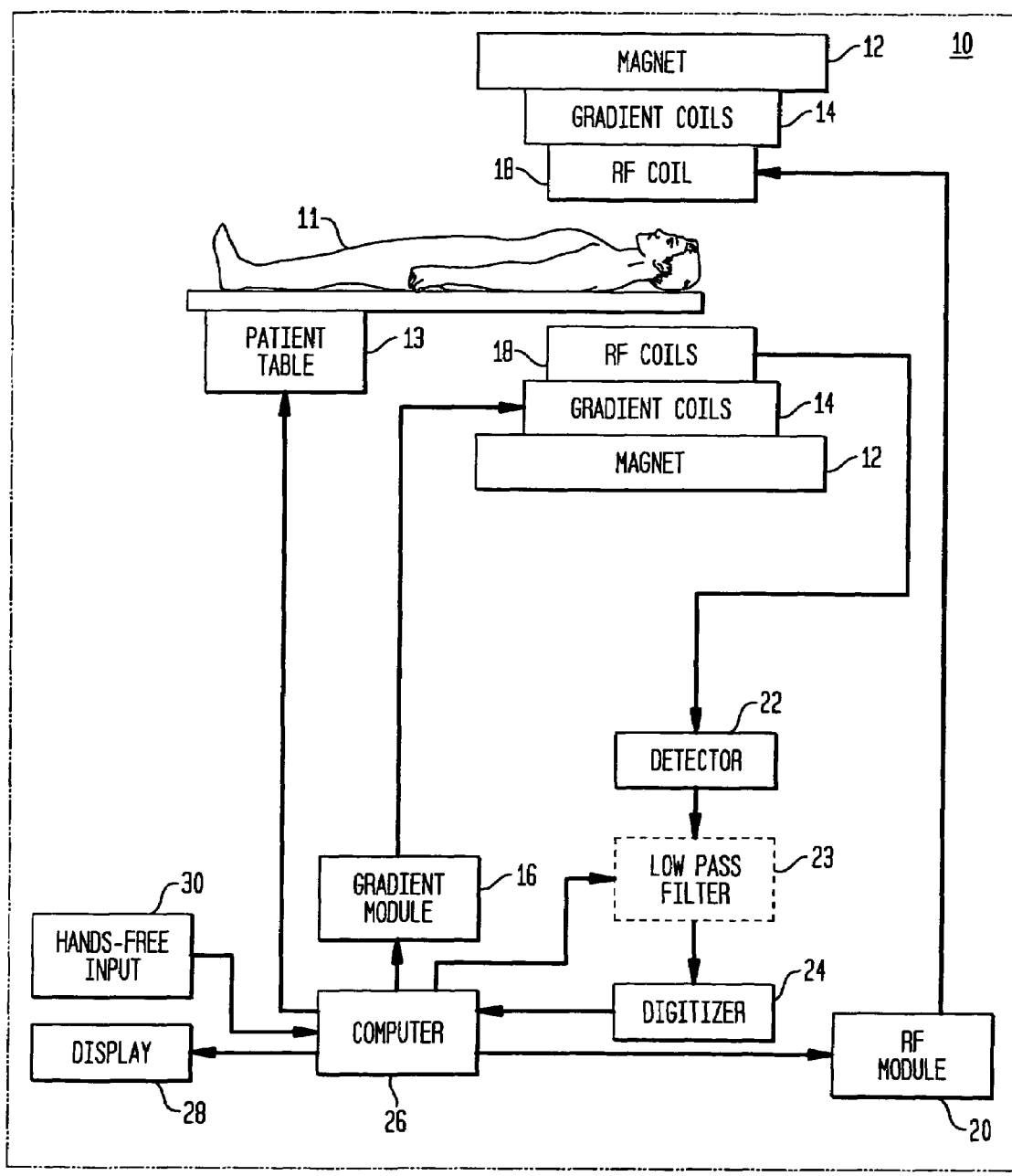
FIG.

RAPID MR VISUALIZATION OF INTERVENTIONAL DEVICES

CROSS-REFERENCE TO RELATED APPLICATIONS

None.

BACKGROUND OF THE INVENTION

1. Field of the Invention

The present invention relates to magnetic resonance (MR) imaging, and more particularly relates to a method and apparatus for more quickly and easily visualizing interventional devices, such as metal-tipped catheters, especially during movement of such devices during an interventional procedure.

2. Description of the Related Art

Known methods of visualizing the movement of catheters by MR imaging typically rapidly acquire data from a thin slab ("slice") of tissue. A ferromagnetic material ("metal") typically located near the distal end (tip) of the catheter causes a local distortion of the otherwise homogeneous magnetic field used by the MR imaging apparatus. If the metal part of the catheter is in or sufficiently near the slice that is currently being imaged, that local distortion of the field causes an image intensity near the position of the metal to be either brighter or darker than normal. This effect of intensity distortion has been used, in a general manner, to help find the catheter as it is moved through the body. For the purpose of visualizing the distal end of the catheter, it is helpful to construct the catheter in such a manner that the tip creates more distortion than the remaining parts. It is also generally known that the size and appearance of the intensity distortion artifact is affected by the precise sequence and timing of the radiofrequency pulses, data collection periods, and magnetic field gradients (i.e., the "pulse sequence parameters") of the MR apparatus. For example, the pulse sequence parameters can be adjusted to produce a strong intensity distortion in response to the metal in the catheter, which spreads over a relatively large spatial area, or a weak intensity distortion that is confined to a small region of the image.

One sequence parameter that affects the intensity of the distortion is the so-called "echo time" or TE, the time between radiofrequency excitation and acquisition of the signal. Another parameter that affects the intensity of the distortion is the strength of the magnetic field gradient applied during the data acquisition (the so called "readout gradient"). It is not common to alter this gradient amplitude by itself, as this would undesirably change the field of view of the reconstructed image along one axis. Instead changes to this gradient amplitude are commonly made in conjunction with changes to several additional sequence parameters, and the net effect is referred to as a change in "receiver bandwidth." Thus, as used herein, the term pulse sequence parameters includes not only the various values of the applied pulse sequence itself, such as the TE duration and readout gradient filed strength, but also the corresponding MR signal processing parameters required to develop an appropriate image in response thereto, such as coordinated analog or digital low pass filtering with an appropriate signal sampling rate, etc.

Under commonly-used conditions, pulse sequences with longer echo times and lower strength readout gradients yield images with increased distortion.

A disadvantage of adjusting the pulse sequence parameters, such as TE or the receiver bandwidth, so as to produce a spatially large distortion is that it may be difficult to localize the exact position of the tip of the catheter. On the other hand, an advantage of this large distortion is that, even if the catheter does not lie precisely in the selected image slab, some distortion will be visible if the catheter is sufficiently near the selected image slab.

The present inventor realized that this distortion effect may in some cases be helpful, because it is not always possible, prior to an image acquisition, to select an image slab that precisely includes the catheter position. A large spatial distortion could allow the catheter tip to be located even when the slab position is imperfect, increasing the ease of tracking the catheter tip as, for example, it is threaded through a vessel.

Even furthermore, it would be advantageous for the physician to have images showing both spatially large and spatially small distortions. To visualize the movement of the catheter, it would be advantageous to obtain multiple images of the same slab of tissue, one after the other, in rapid succession. However, the physician typically does not have time to change pulse sequences or type in new pulse sequence parameters during an interventional procedure, nor have the ability to easily select which images to display.

SUMMARY OF THE INVENTION

A method and apparatus for visualizing an interventional device in a body using a magnetic resonance (MR) imager, which operates in accordance with the following steps:

applying a pulse sequence to the body so as to develop MR signals;

processing the MR signals so that the MR imager acquires one or more images;

wherein parameters of the pulse sequence are preselected so as to cause the images to show an intensity distortion artifact in the area of the interventional device which is increased as compared to intensity distortion artifact in conventional MR images; and after an image distortion which is expected to be produced by the interventional device is seen, an operator of the MR imager controls the pulse sequence parameters, in a "hands-free" manner, so that said one or more acquired images show an intensity distortion artifact in the area of the interventional device that is reduced as compared to said increased intensity distortion.

BRIEF DESCRIPTIONS OF THE DRAWINGS

In order to better understand the invention, the accompanying illustrative and non-limiting drawings, which are incorporated herein and constitute part of this specification, illustrate embodiments and details of the invention, and, together with the general description given above and the detailed description given below, serve to further explain the features of the invention.

The SOLE Figure shows a block diagram illustrating the operation of an MR imaging system 10 which may be used in connection with the method and apparatus of the invention.

DETAILED DESCRIPTION OF THE PREFERRED EMBODIMENTS

The SOLE Figure shows a block diagram illustrating the operation of an MR imaging system 10 which may be used in connection with the method and apparatus of the invention. Since such imagers are well known, only a brief overview description is provided herein. A magnet 12 is provided for creating a static/base magnetic field in a body 11 positioned on a table 13 to be imaged. Within the magnet system are gradient coils 14 for producing position dependent magnetic field gradients superimposed on the static magnetic field. Gradient coils 14, in response to gradient signals supplied thereto by a gradient module 16, produce the position dependent magnetic field gradients in three orthogonal directions. Within the gradient coils is an RF coil 18. An RF module 20 provides RF pulse signals to the RF coil 18, which in response produces magnetic field pulses which rotate the spins of the protons in the imaged body 11 by ninety degrees or by one hundred and eighty degrees for so-called "spin echo" imaging, or by angles less than or equal to 90 degrees for so-called "gradient echo" imaging. In response to the applied RF pulse signals, the RF coil 18 receives MR signals, i.e., signals from the excited protons within the body as they return to an equilibrium position established by the static and gradient magnetic fields, which MR signals are detected by a detector 22 (comprising a preamplifier and amplifier), the MR signals are then filtered by an analog low-pass filter 23 (the pass band of which is controlled directly or indirectly by the pulse sequence and computer 26), converted into digital signals by a digitizer 24 and applied to the MR system computer 26. Alternatively, the function of analog low-pass filter 23 may be carried out by subjecting the digital signals supplied from digitizer 24 to digital filtration algorithms in computer 26. In either case, the term "receiver bandwidth" as used herein refers to the pass band of this MR signal filtration.

In a manner well known to those of ordinary skill in this technology, the gradient magnetic fields are utilized in combination with the RF pulses to encode spatial information into the MR signals emanating from a slice of the body being imaged. Computer 26, using algorithms that are supplied with the details of the pulse sequence, such as the strengths of the applied gradient magnetic fields, adjusts other parameters of the MR imaging system, so as to process the detected MR signals in a coordinated manner to generate high quality images of a selected slab (or slabs) of the body, which images are then shown on a display 28.

In the context of magnetic resonance imaging, modifying a pulse sequence to reduce the parameter commonly referred to as the receiver bandwidth comprises four actions: a reduction in the rate of acquiring samples of the signal, thus changing the sampling bandwidth; a lengthening of the time period (the "readout period") during which the several samples are acquired, so that the total number of samples is unchanged; a reduction of the passband of the analog filter 23, or alternatively reducing the passband of the digital filter that replaces this analog filter; and a reduction in the strength of the magnetic field gradient (the "readout gradient") that is applied during the readout period, thus maintaining the field of view of the image. The latter action directly affects the size of the intensity distortion created by a ferromagnetic object. The resulting pulse sequence is referred to as "low bandwidth," compared to the pulse sequence before such modification ("high bandwidth").

In one embodiment of the invention, two variants of a commonly known and conventional "gradient echo" pulse sequence are employed. In one variant, the pulse sequence parameters are adjusted so that the "receiver bandwidth" is set to be "low," that is, the rate of acquiring samples is relatively low, the duration of the readout period is relatively long, the passband of the low-pass filter is relatively narrow, and perhaps most importantly, the readout gradient amplitude is relatively low, thereby tending to cause the size and intensity of any image distortion created by a ferromagnetic object to be relatively large. In the other variant, the pulse sequence parameters are adjusted so that the "receiver bandwidth" is set to be "high," that is, the rate of acquiring samples during the readout period is high relative to the "low receiver bandwidth" variant, the duration of the readout period is relatively short, the passband of the low-pass filter is relatively wide, and perhaps most importantly, the readout gradient amplitude is relatively high, thereby tending to cause the size and intensity of any image distortion created by a ferromagnetic object to be relatively small in the acquired and reconstructed image. In accordance with this embodiment of the invention, an MR pulse sequence is used that acquires rapid, successive multiple images of the same slab of the body, these images being shown on display 28 nearly in "real-time", while permitting a user-controlled change of the pulse sequence parameters which affect the receiver bandwidth between the acquisition of one image and the next. In a preferred embodiment of this aspect of the invention, a "hands-free" device, such as a foot switch or voice-operated apparatus 30 provides an input to computer 26 to control a switching of the MR imager between the high bandwidth and low bandwidth modes of operation. With this apparatus, the physician can, with minimal interaction, select the artifact visibility that is appropriate for the task at hand.

For example, using the above apparatus, one method which could be used for finding/tracking a catheter in a body, would be to first acquire one or more parallel images at a low receiver bandwidth, in order to see if an image disturbance caused by the tip of the catheter can be seen. During this initial phase, the physician can use the hands-free device 30 to instruct computer 26 to display images of successive positioned parallel slabs in a given direction, at say 5mm each, for example by saying "plus . . . plus . . . " into a voice-activated version of the hands free device 30. When a maximum artifact is seen, the physician can then issue a voice command to device 30 to switch to the higher receiver bandwidth to get a sharp view of the current position of the catheter tip. Alternatively, for activating this command, the hands-free device 30 could comprise a foot-activated switch.

To reduce the guesswork involved with following the motion of the catheter through successively positioned parallel slabs, a command to the hands-free device 30 could direct computer 26 to adjust the pulse sequence parameters so as to image a plane that is normal to the plane of the current slab, and passes through the current position of the artifact, and then, in this normal direction, search successive positioned parallel slabs in the plus or minus direction until the catheter artifact is again acquired maximally. As the catheter is moved further, the process can be repeated in a further plane that is normal to the plane of the currently imaged slab. More specifically, the physician can start, for example, with a coronal image at low receiver bandwidth and search plus and minus parallel slabs until the catheter artifact is found. Then, the physician can position an orthogonal slice (i.e., an axial slice) through the middle of the artifact. When this image is displayed, the physician can use it to position an orthogonal slice (coronal or sagittal) through the large artifact. At any time during the flip-flopping of image views, the physician can switch to the higher receiver bandwidth to get a sharp image of the catheter tip and surrounding tissue. Switching between orthogonal planes, plus/minus repositioning of the imaging slab, and switching of the receiver bandwidth, should preferable all be done using commands (foot switch or voice-operated) to the hands-free device 30.

In a further embodiment of the invention, two variants of a gradient echo pulse sequence with different values for less than all of the parameters that comprise those defined above for "receiver bandwidth" can be used, however such differences may lead to images that are different in more respects than just the intensity of the artifact distortion. For example, perhaps only the strength of the readout gradient or the duration of the TE interval is changed. Such changes may still yield useful images.

In a further embodiment of the invention, gradient echo pulse sequence parameters are employed which form two gradient echoes for each RF excitation, one which is received with high bandwidth and one which is received with low bandwidth, for producing two images of the same slab. In one variation of this embodiment, to simplify the image display, only one of these images is displayed to the physician per acquisition, either the first ("shorter") echo (high bandwidth) image with a potentially small spatial artifact, or the second ("longer") echo (lower bandwidth) image with the potentially larger spatial artifact. The physician can use the hands-free (foot switch or voice-operated) apparatus 30 to switch between display of one of these images.

In an even further embodiment of the invention, a similar gradient echo pulse sequence is employed for producing the low and high bandwidth images of the same slab. In this embodiment, however, both images are displayed to the physician simultaneously, side-by-side, on display 28.

In a still further embodiment of the invention, a different type of pulse sequence can be used to obtain the successive images. For example, a "spin echo" pulse sequence can be used to obtain images with spatially small metal artifact distortions, while a gradient echo pulse sequence can be used to obtain low bandwidth images with spatially larger distortions. The hands-free apparatus 30 can be used to toggle the operation of the MR imager between this spin echo sequence and the low bandwidth gradient echo pulse sequence.

For the purposes of promoting an understanding of the principles of the invention, reference has been made to the preferred embodiments illustrated by the drawing, and specific language has been used to describe these embodiments. However, this specific language is not intended to limit the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional electronics, control systems, and other functional aspects of the systems (and components of the individual operating components of the systems) may not be described in detail. Furthermore, the connecting lines, or connectors shown in the figure are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

For example, the hands-free apparatus 30 can be used to allow the selection of a number of receiver bandwidths that are greater than two, thereby allowing more control of over visualization of the metal artifact. Furthermore, the hands-free apparatus 30 can include both of the foot switch and the voice-recognition inputs. Even further, many other ways could be devised in order to produce the lower or higher bandwidth images.

Accordingly, it is intended that the present invention not be limited to the described embodiments, but that it has the full scope defined by the above language and the following claims, as well as equivalents thereof.

The following claims provide further details concerning the elements, actions, and/or steps that are contemplated as falling within the scope of the methods and apparatus of the present invention.

What is claimed is:

1. A method for identifying and enhancing visualization of an interventional device using a magnetic resonance (MR) imaging system, comprising the following steps:

employing a pulse sequence in MR imaging a body portion of a patient and deriving response MR signals for use in providing MR images of said body portion;

processing the MR signals to provide MR images of said body portion, in response to first parameters of the applied pulse sequence predetermined for acquisition of a first gradient echo image, using a first amplitude readout gradient and first receiver bandwidth, said first gradient echo image including a first intensity distortion artifact in the area of an interventional device and second parameters of the applied pulse sequence predetermined for acquisition of a second gradient echo image, using a second amplitude readout gradient and second receiver bandwidth, said second gradient echo image including a second intensity distortion artifact in the area of an interventional device, said first parameters providing a relatively low amplitude readout gradient and relatively low receiver bandwidth and increased spatial image intensity distortion artifact compared to said second parameters and are selected to facilitate locating said interventional device relative to an image slab; and selecting either said first or second parameters in response to user command.

2. The method of claim 1, including using a hands-free device for controlling selection of said first and second parameters to selectively acquire gradient echo images using a relatively long echo time to show said increased spatial image intensity distortion artifact, and selectively acquire gradient echo images using a relatively short echo time to show a reduced intensity distortion artifact.

3. The method of claim 1, including using a hands-free device for controlling selection of said first and second parameters to selectively acquire gradient echo images using a relatively low amplitude readout gradient, relatively low receiver bandwidth, and relatively long echo time to show said increased spatial image intensity distortion artifact, and selectively acquire gradient echo images using a relatively high amplitude readout gradient, relatively high receiver bandwidth, and relatively short echo time to show a reduced intensity distortion artifact.

4. The method of claim 1, including using a hands-free device for controlling selection of said first and second parameters selectively acquire gradient echo images using a relatively low amplitude readout gradient, relatively low receiver bandwidth, and relatively long echo time a person who guides the interventional device in the body to show said increased spatial image intensity distortion artifact, and selectively acquire spin echo images so as to show a reduced intensity distortion artifact.

5. The method of claim 1, including the step of, in response to user command, alternating between acquisition of a sequence of images with reduced image intensity distortion, and acquisition of a sequence of images with increased spatial image intensity distortion in the area of the interventional device.

6. The method of claim 1, wherein in response to user hands-free command to adjust the parameters of the MR imaging system, images which show increased spatial image intensity distortion are acquired, as a sequence of parallel images, and are moved in a positive or negative spatial direction until an image slab is found where the intensity distortion artifact appears to be at or near a maximum and one or more images which show reduced image intensity distortion are acquired.

7. The method of claim 1, wherein in response to user hands-free command to adjust the parameters of the MR imaging system, images that show increased spatial image intensity distortion are acquired, as a sequence of orthogonal images, and image slab location is moved in a positive or negative spatial direction, until an image slab is found where the image intensity distortion appears to be at or near a maximum and images are acquired which show reduced image intensity distortion.

8. The method of claim 1, including enabling use of a hands-free device comprising at least one of, (a) a foot activated switch and (b) voice recognition circuitry to provide a hands-free instruction input to control the operation of the MR imaging system.

9. The method of claim 1, including enabling use of a hands-free device for controlling the sequence parameters of the MR imaging system so as to selectively acquire the images which show said increased spatial image intensity distortion artifact, a reduced spatial image intensity distortion artifact, or an intensity distortion artifact between the reduced and increased spatial image intensity distortion artifact.

10. The method of claim 1, wherein said employing step comprises employing both gradient pulses and RF pulses to the patient body, and a gradient echo pulse sequence which produces two images for each RF pulse applied to the body, one image showing an increased spatial image intensity distortion artifact and the other image showing a reduced spatial image intensity distortion artifact.

11. The method of claim 10, including enabling use of a hands-free device to control which image is displayed on a display portion of the MR imaging system.

12. The method of claim 10, further comprising displaying both images concurrently on a display portion of the MR imaging system.

13. The system according to claim 1, including the steps of:
applying to the body a pulse sequence which produces two images for each RF pulse excitation applied to the body, one image being acquired by the MR imaging system with a relatively low readout gradient amplitude and relatively low receiver bandwidth and the other image being acquired by the MR imager with a relatively high readout gradient and relatively high receiver bandwidth; and
displaying the images by at least one of,
a) displaying both images concurrently side by side on a display of the MR imaging system, and
b) using a hands-free input device to control the MR imaging system to present one of said images on the display at a time.

14. A system for identifying and enhancing visualization of an interventional device in magnetic resonance (MR) medical images of a portion of a patient body, comprising:
an MR imaging system including a computer for,
employing a pulse sequence in MR imaging a body portion of a patient and deriving response MR signals for use in providing MR images of said body portion;
processing the MR signals to provide MR images of said body portion, in response to,
a first set of parameters of the applied pulse sequence predetermined for acquisition of a first gradient echo image, using a first amplitude readout gradient and first receiver bandwidth, said first gradient echo image including a first intensity distortion artifact in the area of an interventional device and
a second set of parameters of the applied pulse sequence predetermined for acquisition of a second gradient echo image, using a second amplitude readout gradient and second receiver bandwidth, said second gradient echo image incorporating a second intensity distortion artifact in the area of an interventional device, said first set of parameters providing a relatively low amplitude readout gradient and relatively low receiver bandwidth and increased image intensity distortion artifact compared to said second set of parameters and are selected to facilitate locating said interventional device relative to an image slab, said first and second set of parameters being individually selectable in response to user command; and
a user interface device for providing data for selecting between said first and second set of parameters in response to user command.

15. The system according to claim 14, wherein
said second set of parameters provide a relatively high amplitude readout gradient and relatively high receiver bandwidth and reduced spatial image intensity distortion artifact compared to said first set of parameters and supports more accurate tracking of said interventional device relative to said first set of parameters.

16. The system according to claim 15, wherein
said user interface device provides said data for selecting between said first and second set of parameters in response to user hands-free command.

* * * * *